United States Patent
Abkai et al.

(10) Patent No.: US 10,478,089 B2
(45) Date of Patent: Nov. 19, 2019

(54) METHOD FOR CAPTURING A DENTAL OBJECT

(71) Applicant: DENTSPLY SIRONA Inc., York, PA (US)

(72) Inventors: Ciamak Abkai, Heddesheim (DE); Tim Braun, Grob-Gerau (DE); Jan Paul, Ulm (DE); Volker Rasche, Erbach (DE)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 15/837,233

(22) Filed: Dec. 11, 2017

(65) Prior Publication Data

US 2018/0160932 A1 Jun. 14, 2018

(30) Foreign Application Priority Data

Dec. 12, 2016 (DE) ................................ 16203381.5

(51) Int. Cl.
*G06K 9/00* (2006.01)
*A61B 6/14* (2006.01)
(Continued)

(52) U.S. Cl.
CPC ............ *A61B 5/055* (2013.01); *A61B 5/4547* (2013.01); *A61B 5/7278* (2013.01); *A61B 5/742* (2013.01);
(Continued)

(58) Field of Classification Search
USPC ........ 382/100, 103, 106–107, 128–133, 154, 382/162, 168, 173, 181, 189, 199, 209,
(Continued)

(56) References Cited

U.S. PATENT DOCUMENTS

2009/0041191 A1* 2/2009 Suzuki ................... A61B 6/14
378/98.5
2009/0128553 A1 5/2009 Perry et al.
(Continued)

FOREIGN PATENT DOCUMENTS

EP 2511725 A1 10/2012
JP 2003113096 A 4/2003

OTHER PUBLICATIONS

Benedikt A. Poser, "Simultaneous Multi-Slice Excitation by Parallel Transmission", Magn Reson Med. Apr. 2014; 71(4); 1416-1427.

*Primary Examiner* — Seyed H Azarian
(74) *Attorney, Agent, or Firm* — Dentsply Sirona Inc.

(57) ABSTRACT

Disclosed herein is a method for capturing a dental object with an object volume, in particular, at least one part of a maxilla and/or a mandible, with the sue of an MRT apparatus. A plurality of MRT segment images, which depict the defined segmented volume regions are acquired by an MRT apparatus within a measurement volume of the MRT apparatus. The segmented volume regions overlap no more than partially. In this case a target surface is defined or has already been defined. Then a two dimensional composite image, which corresponds to a two dimensional aggregate image through the target surface within the object volume of the dental object, is generated computer-aided from the individual MRT segment images.

14 Claims, 1 Drawing Sheet

(51) Int. Cl.
*A61B 5/055* (2006.01)
*A61C 9/00* (2006.01)
*A61B 5/00* (2006.01)
*G06T 5/50* (2006.01)
*G06T 7/00* (2017.01)
*G06T 11/00* (2006.01)

(52) U.S. Cl.
CPC .............. *A61B 6/14* (2013.01); *A61C 9/0046* (2013.01); *G06T 5/50* (2013.01); *G06T 7/0014* (2013.01); *G06T 11/008* (2013.01); *A61B 5/7425* (2013.01); *A61B 2576/02* (2013.01); *G06T 2207/10088* (2013.01); *G06T 2207/10116* (2013.01); *G06T 2207/30036* (2013.01)

(58) Field of Classification Search
USPC ..... 382/224, 232, 254, 27, 4, 276, 285–291, 382/305, 312; 345/424; 433/24; 1/1; 378/98.5, 38
See application file for complete search history.

(56) References Cited

U.S. PATENT DOCUMENTS

| | | | |
|---|---|---|---|
| 2011/0268327 A1* | 11/2011 | Getto | G09B 23/283 382/128 |
| 2012/0015316 A1* | 1/2012 | Sachdeva | G06T 17/00 433/24 |
| 2013/0162645 A1* | 6/2013 | Ulrici | A61B 6/032 345/424 |
| 2013/0252196 A1 | 9/2013 | Rasche et al. | |
| 2016/0310097 A1* | 10/2016 | Bae | A61B 6/032 |

* cited by examiner

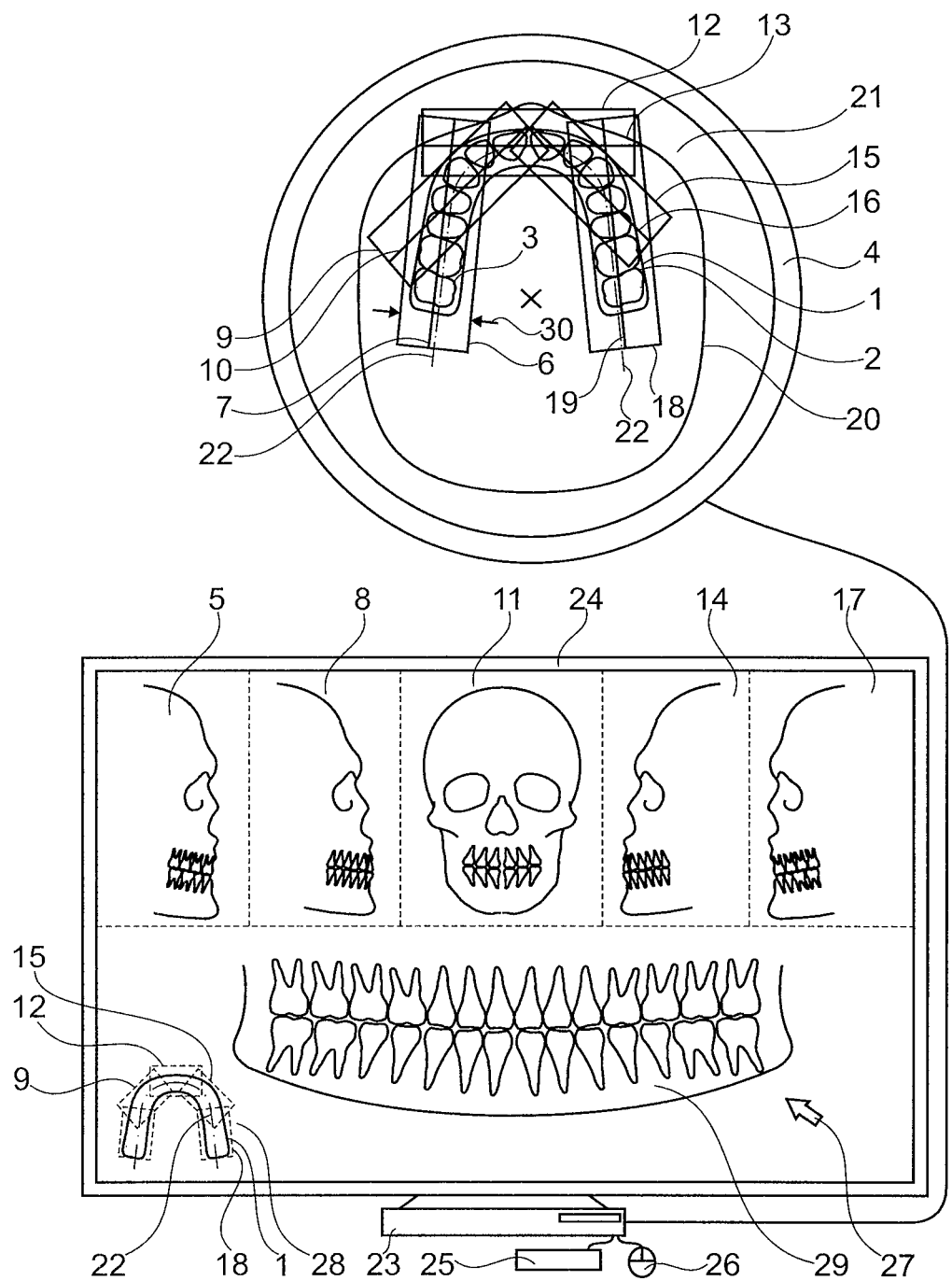

METHOD FOR CAPTURING A DENTAL OBJECT

TECHNICAL FIELD

Disclosed herein is a method for capturing a dental object with an object volume, in particular, at least one part of a maxilla and/or a mandible, by means of an MRT apparatus, wherein a plurality of MRT segment images, which depict the defined segmented volume regions, are acquired by means of the MRT apparatus within a measurement volume of the MRT apparatus, wherein the segmented volume regions overlap no more than partially.

BACKGROUND

The prior art discloses a number of methods for creating MRT images of dental objects or parts thereof, such as the upper jaw/lower jaw.

According to one known method, a conventional MRT apparatus is used to obtain individual MRT cross sectional images, which cut, for example, the jaw arch. If the objective were to acquire the entire jaw arch, then, for example, five individual MRT cross sectional images would be necessary.

One disadvantage of this method lies in the fact that the manual planning of the individual MRT cross sectional images is associated with a considerable amount of time. The individual MRT cross sectional images are not contiguous and, thus, render the diagnosis difficult.

According to another method, the so-called curved MPR method, first an approximately isotropic volume data set is acquired by means of a conventional MRT apparatus; and then this volume data set is projected by means of a computer along a manually drawn curved path over the jaw arch, a so-called panoramic curve; and, in so doing, a two dimensional production image of the whole jaw arch is generated.

One drawback with this method is that the sampling of an isotropic volume data set is associated with a considerably longer image acquisition time as compared to the individual MRT cross sectional images. In addition, the image quality of the volume data set is degraded by the subsequent image manipulation, in particular, due to an interpolation loss.

Therefore, one object of the present disclosure is to provide a method for capturing a dental object in such a way that the image acquisition time is shortened and the image quality is improved so that there is no need for additional hardware components, as is the case with a conventional MRT apparatus.

SUMMARY

Disclosed herein is a method for capturing a dental object with an object volume, in particular, at least one part of a maxilla and/or a mandible, by means of an MRT apparatus, wherein a plurality of MRT segment images, which depict the respectively defined segmented volume regions, are acquired by means of the MRT apparatus within a measurement volume of the MRT apparatus. In this context the segmented volume regions overlap no more than partially. A target surface is defined or has already been defined. A two dimensional composite image, which corresponds to a two dimensional aggregate image through the target surface within the object volume of the dental object, is generated from the individual MRT segment images by means of a computer.

The dental object may be at least a part of the upper jaw and/or lower jaw. The dental object may also include several, non-contiguous regions of the upper jaw and/or the lower jaw. The jaw joints may also be a part of the dental object. The MRT apparatus (magnetic resonance tomography apparatus) is a conventional MRT apparatus for scanning a head, in particular, an upper jaw and/or a lower jaw. In this case the MRT apparatus has a measurement volume, and the object volume of the object is arranged within the measurement volume, in order to be able to sample the object. According to the present method, a plurality of MRT segment images, i.e., at least two MRT segment images, are acquired by means of the MRT apparatus, with each of the MRT segment images depicting a defined segmented volume region. The segmented volume regions may have any arbitrary shape and may have, for example, a cubic geometry.

The segmented volume regions of the individual MRT segment images may also have a curved shape; and in this case a special MRT apparatus is used that can acquire such a curved segmented volume region. In such an MRT apparatus the gradient coils may be arranged, for example, in such a way that the isolines of a gradient field extend in a curved shape.

An MRT segment image may include a single MRT slice image, so that the MRT segment image is acquired in one step by means of the MRT apparatus. In this way the individual MRT segment images are sampled one after the other in succession. As an alternative, another MRT apparatus may be used that can acquire the MRT segment images simultaneously. In this case such an MRT apparatus permits the excitation of a plurality of slices in the object volume and is based on a so-called multi-pulse excitation method, which is described in the following professional article (Benedikt A. Poser. Simultaneous Multi-Slice Excitation by Parallel Transmission. Magn Reson Med. 2014 April; 71 (4); 1416-1427).

In the case of a conventional MRT apparatus the sampling is performed within the object volume along an X gradient, along a Y gradient, and along a Z gradient; and the resolution is set by adjusting a length, a width and a depth of a voxel within the object volume by controlling the gradient coils accordingly. A typical resolution is determined by means of a voxel having a length of 0.5 mm, a width of 0.5 mm and a depth between 1.5 mm and 15 mm.

The length and the width of a voxel may range from 0.3 mm to 2 mm, so that the resolution of the MRT segment image is determined by sampling the individual voxel.

The present method may use, for example, a particular addressing of the MRT apparatus that generates a particular RF pulse (2D pulse) in order to excite curved volume regions that are then read out as planar projections. Therefore, the technical possibilities of a conventional MRT apparatus are sufficient for this purpose.

The present method can also use a conventional 1D RF pulse as the excitation pulse that has, as compared to the 2D pulse technique, the advantage of faster imaging and less sensitivity to magnetic field interferences, for example, due to metals or air. Such interferences due to metal parts and air may occur, in particular, in the region of the maxilla and the mandible.

The MRT apparatus that is employed may also be based on an MRT method, with which spatially curved regions of the same magnetic field strength are generated by means of special, additional non-linear gradient coils in the measurement volume, in order to both excite curved volume regions and also to read out in an imaging manner, as disclosed in EP 2 511 725 A1.

The method may also use a conventional MRT apparatus, which has conventional gradient coils with straight isolines of the gradient fields. As a result, there is no need to install additional gradient coils, so that not only is the measurement volume of the MRT apparatus not reduced, but the higher costs of retrofitting the MRT apparatus are also avoided. Therefore, the present method can be carried out by means of a conventional MRT apparatus without having to adapt the MRT apparatus in any special way.

In this respect the segmented volume regions are defined in such a way that they overlap no more than partially. Thus, the segmented volume regions may be arranged in such a way that they include the object only to some extent; and gaps are produced between the object volume regions; or the segmented volume regions may overlap partially, so that at least one part of the object is captured continuously. The segmented volume regions may be defined automatically or may be defined by a user.

The segmented volume regions may overlap, but are not fully mutually inclusive. As an alternative, the segmented volume regions may be arranged in such a way that gaps are generated when sampling the object. The segmented volume regions may also cover only a portion of a jaw.

The segmented volume regions may also be acquired with a different resolution, so that the MRT segment images that are generated also have different resolutions.

In order to carry out the present method, the target surface may already be defined in relation to the MRT apparatus or may be defined computer-aided or by a user. The two dimensional composite image is created from the individual MRT segment images; and said two dimensional composite image corresponds to the two dimensional aggregate image through the target surface. Therefore, the aggregate image corresponds to a mapping of the MRT segment images on the target surface.

The target surface may be arranged to follow, for example, the contour of the maxilla and/or the mandible, so that the composite image corresponds to or simulates a conventional panoramic slice image from X-ray diagnostics.

Thus, in analogy to a panoramic slice image from X-ray diagnostics, the position and orientation of the sharp slice are defined by defining the target surface.

The target surface may be, for example, a mid-surface of the object volume, which may be defined by the mid-planes of the individual segmented volume regions or may be defined by the mid-surface of an anatomical structure, such as a jaw.

Each of the MRT segment images may be a three dimensional image or a two dimensional image. If the MRT segment image is a three dimensional image, then the individual voxels of the MRT segment image are projected into a direction of projection, which may be arranged, for example, orthogonal to the target surface, onto the target surface, in order to create the composite image. During production the single voxel may also be weighted by a fixed weighting factor. If the single MRT segment image is a two dimensional image, then each pixel of the MRT segment image is projected directly onto the target surface.

Therefore, the two dimensional image has only one slice of voxels along one of the axes of the respective segmented volume region, while the three dimensional image has a plurality of voxels along all of the axes of the respective segmented volume region. The projection is carried out by projecting the available voxels (one slice or several slices) of the respective segmented volume region along one direction of projection, which may be arranged, for example, perpendicular to the target surface, onto the target surface and may be aggregated.

The target surface may be defined or may have already been defined prior to defining the segmented volume regions in the object volume, so that the segmented volume regions are arranged as a function of the known target surface. The segmented volume regions may be arranged, for example, in such a way that the target surface is contained at least partially therein.

After defining or even after sampling the segmented volume regions, the target surface may also be shifted subsequently, in relation to the MRT apparatus, within the measurement volume and/or in relation to the segmented volume regions. The target surface may also be adapted subsequently, for example, as a function of the defined segmented volume regions.

One advantage of the present method is that in order to capture the dental object, only individual MRT segment images along the jaw arch have to be acquired, and the composite image is fitted together, for example, by projecting the MRT segment images onto the target curve. Therefore, compared to the curved MPR method, the entire volume data set of the tooth situation does not have to acquired; and subsequently a volume region for the panoramic curve can be selected manually from the volume data set. This aspects shortens the image acquisition time for carrying out the method.

A depth of each of the segmented volume regions can be defined in an advantageous way, where in this case each segmented volume region is defined with respect to its position and orientation within the measurement volume.

As a result, the position and orientation of the individual segmented volume regions within the measurement volume of the MRT apparatus are defined. The segmented volume regions may be arranged, for example, in such a way that in a children's program the individual segmented volume regions are sampled automatically along a maxilla and/or a mandible of an average patient head of a child. In an adult program the segmented volume regions are then arranged correspondingly in such a way that the segmented volume regions are sampled along a maxilla and/or a mandible of an average patient head of an adult.

Then the user may select a matching program on the MRT apparatus.

The depth of the segmented volume region may range advantageously from 0.5 mm to 30 mm, such as from 1 mm to 15 mm.

Thus, the maxilla and/or the mandible is/are totally contained within the segmented volume region and is/are correspondingly completely imaged as a projection in the composite image.

The depth of a cube-shaped, segmented volume region may be arranged, for example, in an orthogonal direction in relation to the target surface. The length and the width of the segmented volume region may be selected in such a way that the object is contained therein.

Advantageously each of the MRT segment images may depict a segmented volume region having a cubic shape or a longitudinally segmented volume region having a curved shape.

The geometry of the segmented volume region is influenced by the design of the MRT apparatus and, in particular, the gradient coils of the MRT apparatus.

In the case of a conventional MRT apparatus three gradient coils are used that generate linear gradient fields along the x, y, z axes of a patient's opening. This arrangement allows a planar surface, which can be rotated arbitrarily, to obtain a unique resonance frequency through superimposition of the gradient fields. The excitation region by means of the conventional 1D pulse is the excited planar surface extruded along the three surface axes and, thus, represents a cube, which is oriented arbitrarily in space.

The target surface of the two dimensional composite image may be advantageously a curved target surface, which extends through the maxilla and/or the mandible of a sample head or a preview image of the patient's head.

As a result, the two dimensional composite image is created as a cross sectional image through the target surface, so that the composite image corresponds to a conventional panoramic slice image from X-ray diagnostics.

In this case the position and orientation of the curved target surface within the measurement volume of the MRT apparatus are specified by the arrangement of the maxilla and/or the mandible of the sample head (of a child or an adult) or by the preview image of the patient's head. Thus, the MRT apparatus is gradually adjusted in such a way that the defined segmented volume regions are sampled one after the other in succession; and the MRT segment images are projected on the defined target surface.

The preview image of the patient's head may be, for example, a three dimensional X-ray image or a three dimensional MRT image of the patient's head of the respective patient.

The preview image of the patient's head may also be a two dimensional X-ray image or a two dimensional MRT image, which permits the positioning of the target surface.

Thus, the target surface is defined through the use of a sample head (3D model of a head) or a preview image of the head (patient oriented planning image). The fixing of the patient relative to the MRT apparatus may be carried out, for example, by means of a head holder and/or a bite holder.

Advantageously the target surface may be planar in shape in a direction perpendicular to an occlusal plane of the maxilla and/or the mandible or in one direction may be curved in shape, tracking the course of the tooth axes of the maxilla and/or the mandible.

Thus, in a first alternative the target surface is curved in shape along the maxilla and is planar in shape in the direction perpendicular to the occlusal plane. In the second alternative the target surface is curved in shape, tracking the tooth axes in both an approximal direction along the course of the jaw and also in the occlusal direction of the tooth axes. Thus, in the two alternatives one composite image through the target surface is created that depicts very clearly the maxilla and/or the mandible.

The occlusal plane describes the spatial plane, on which the teeth of the upper and lower jaw meet. Said occlusal plane is constructed by the connecting lines between the incisal point (contact point of the cutting edges of the teeth 31 and 41) and the distobuccal cusp of the teeth 36 and 41 and usually extends through the lip seal line.

The tooth longitudinal axis of a tooth is referred to as the tooth axis. Said tooth axis is defined as the connecting line between the root apex in singled rooted teeth and the center of the cutting edge and in multirooted teeth between the root furcation (bifurcation, trifurcation) and the occlusal surface center. The tooth axes of the anterior teeth (cuspids and incisors) in the maxilla are inclined in the distal direction in the normal position.

Advantageously the composite image may correspond to a conventional X-ray panoramic slice image.

Advantageously the target surface of the composite image may correspond to or simulate the course of a sharp slice of a conventional X-ray panoramic slice image.

As a result, the composite image corresponds to a conventional X-ray panoramic slice image and makes it easier for a dentist to make a diagnosis, as customary, by means of a panoramic slice image.

Advantageously the composite image can be created from the individual MRT segment images by determining for each pixel of the composite image on the target surface the position of the center point of this pixel. For each voxel or pixel of one of the MRT segment images the center point is determined, and this center point is projected along a known direction of projection of the respective MRT segment image onto the target surface, in order to determine a projected center point. For a composite image pixel of the composite image that voxel or pixel of one of the MRT segment images is used whose projected center point is arranged the closest to the center point of the respective composite image pixel.

Thus, the target surface may extend through the central planes of the MRT segment images and at the intersecting lines of the central plane of an MRT segment image may change places with the respectively adjacent MRT segment image on the adjacent central plane. If on the basis of this target surface definition, each composite image pixel is allocated exactly one specific voxel of one of the MRT segment images, then the result may be visually abrupt changes in the pixel values ("creases") at the transitions between the central planes of the individual MRT segment images in the composite image due to the varying orientations of the MRT segment images. One advantage of this embodiment consists of the feature that an individual MRT segment image is not distorted, and the anatomical structures within the MRT segment image are reproduced true to scale in the composite image.

Those pixels or voxels of an MRT segment image are used advantageously as the composite image pixel whose distance between the projected center point of this pixel or voxel and the center point of the composite image pixel is less than a defined tolerance value; and/or in the event that an angle between a desired direction of projection of the composite image pixel and a direction of projection of this pixel or voxel is less than a defined maximum angle.

The desired direction of projection of the composite image pixel may be arranged, for example, orthogonal to the target surface. In this case the actual direction of projection of the pixel or voxel is specified by means of the orientation of the MRT segment image, in particular, by means of the direction of the Z gradient.

As an alternative, when creating the composite image from the individual MRT segment images, the MRT segment images may be projected onto the target surface by determining for each pixel of the composite image on the target surface the position of a center point of this pixel. For each pixel or voxel of one of the MRT segment images a center point is determined, with this center point being projected along a known direction of projection of the respective MRT segment image onto the target surface, in order to determine a projected center point, so that the result is a composite image pixel of the composite image through interpolation of at least two adjacent, projected pixels or voxels of the MRT segment images.

In this alternative embodiment the composite image is created through interpolation of the adjacent pixels of the MRT segment images. One advantage of these alternative embodiments consists of the feature that visually fewer noticeable transitions, thus, small creases, are generated at the transitions between the MRT segment images.

Advantageously prior to creating or sampling the MRT segment images, the number of MRT segment images, the position and/or the orientation of the MRT segment images relative to the MRT apparatus can be fixed automatically or to some extent automatically by means of a computer.

In this way the number, the position and the orientation of the MRT segment images are determined automatically by means of the computer. In the event that the object is, for example, the left side of the upper jaw, two or three segmented volume regions can be automatically determined that partially overlap and totally contain the left upper jaw.

In the automatic planning the object volume, containing the maxilla and/or the mandible, may be automatically divided into 3 to 30 segmented volume regions, such as 6 to 8 segmented volume regions. In this case the segmented volume regions are arranged with respect to each other in such a way that they are uniformly divided along the maxilla or the mandible and allow the object volume to be captured in its entirety.

Advantageously each of the segmented volume regions within the object volume may be arranged in such a way that a central plane of the respective segmented volume region is arranged parallel to a tangent of the target surface.

As a result, the individual segmented volume regions are arranged as a function of the already defined target surface in such a way that the respective central plane of the segmented volume region is arranged tangential to the target surface. The central plane of a segmented volume region may correspond, for example, to a direction of the respective MRT segment image, which may be specified by a longest edge or a largest lateral surface of the cube-shaped, segmented volume region.

Each of the segmented volume regions may be arranged advantageously in such a way that a direction of the lowest resolution of the respective MRT segment image is arranged orthogonal to the target surface.

In this way the MRT segment images are projected in the direction of the lowest resolution onto the target surface, so that the two dimensional composite image has a higher resolution.

In the case of a conventional MRT apparatus the sampling within the object volume takes place along an X gradient, along a Y gradient and along a Z gradient, and the resolution is set by adjusting a length, a width and a depth of a voxel within the object volume. A typical resolution is determined by a voxel having a length of 0.5 mm, a width of 0.5 mm and a depth between 1.5 mm and 15 mm. The direction of the depth of the voxel agrees correspondingly with the direction of the lowest resolution of the respective MRT segment image.

Advantageously the number, the position and/or the orientation of the segmented volume regions may be varied by means of an optimization method, until an error size falls below a fixed tolerance value.

As a result, the number, the position and the orientation of the segmented volume regions within the measurement volume of the MRT apparatus are determined automatically by means of the optimization method. Thus, the amount of time required to plan the individual segmented volume regions is shortened.

Advantageously the error size that may be used includes the sum of the angles between an actual direction of projection and a desired direction of projection of the individual composite image pixels of the composite image, where in this case the desired direction of projection corresponds to a normal relative to the target surface, and the actual direction of projection is defined by means of the direction of projection of the pixel or voxel that is used from the respective MRT segment image.

In this way the optimization method ensures that the fixed tolerance value of the error size is not exceeded, because in the event that the number of the segmented volume regions is too small, distinct creases or distortions may be generated in the composite image at the transition zones between the individual MRT segment images, since the actual direction of projection deviates significantly from the desired direction of projection, in particular, at the transition zones.

Advantageously the number of MRT segment images, the position and/or the orientation of the MRT segment images relative to the MRT apparatus can be defined by a user prior to creating the MRT segment images, where in this case a virtual tool may be used to define the position and the orientation of the segmented volume regions of the MRT segment images relative to the MRT apparatus.

Thus, the individual segmented volume regions may be virtually defined by the user.

The fixing of the segmented volume regions may also be carried out to some extent automatically, so that a temporary position and orientation of the segmented volume regions are suggested in the first step and may be corrected by the user by means of a virtual tool in the second step.

In this context the virtual tool may be any computer algorithm that permits interaction between the user and the segmented volume regions.

Advantageously a sample head comprising a sample maxilla and/or a sample mandible may be displayed in schematic form by means of a display device, where in this case the defined segmented volume regions and their arrangement relative to the sample head and/or the defined target surface relative to the sample head are represented graphically.

In this way the user is shown graphically the points, at which the segmented volume regions and the defined target surface relative to the sample head are located. This feature makes it easier for the user to analyze the composite image that is created.

The transitions between the MRT segment images may also be shown visually by means of the display device.

The composite image that is created may also be superimposed onto a two dimensional or three dimensional model of a sample head or a patient oriented preview image, in order to allow the user an orientation relative to the structures outside the jaw, such as the skull. The region, on which the composite image is superimposed, may be punched virtually out of the model of the sample head or the patient oriented preview image, so that the composite image is not overlaid with the background.

Advantageously the display device can be used to show the composite image that is created and the sample head simultaneously with the graphic representation of the individual segmented volume regions and/or with the defined target surface (22).

This aspect makes it easier for the user to use the sample head as a reference and, in so doing, to better diagnose the composite image that is created.

Advantageously each MRT segment image may consist of a single MRT slice image or a stack of several MRT slice images.

Therefore, this feature allows the MRT segment image to be made up of a single stack of several MRT slice images, so that the MRT segment image is acquired in one step by means of the MRT apparatus or in multiple steps that follow one after the other in succession.

Advantageously the MRT slice images of a stack can be arranged parallel to each other perpendicular to a fixed direction of acquisition.

This aspect allows each of the MRT slice images to be sampled slice by slice one after the other.

Advantageously the spatial position of the dental object relative to the measurement volume of the MRT apparatus remains the same in all of the MRT segment images.

Thus, the dental object, such as a patient's head, is positioned so as to be fixed with respect to the MRT apparatus; and then the individual MRT segment images are acquired.

In the case of a known method, for example, for sampling the vertebral column, a plurality of MRT images are taken, where in this case the patient is moved with respect to the MRT apparatus between the MRT image taking.

One advantage of a fixed positioning of the object relative to the MRT apparatus is that the position of the object relative to the MRT apparatus is exactly the same in all of the MRT segment images; and, when computing the various images, there are no additional spatial inaccuracies caused by the patient being moved. Furthermore, an increase in the total image acquisition time owing to the mechanical shift is avoided, and the workflow for the MRT technician is kept simple.

BRIEF DESCRIPTION OF THE DRAWINGS

The present disclosure is explained below with reference to the drawings. The drawings show in FIG. 1 a sketch to elucidate the present method.

DETAILED DESCRIPTION

FIG. 1 shows a sketch to elucidate the present method for capturing a dental object 1, in particular, at least one part of a maxilla 2 and/or a mandible 3 by means of an MRT apparatus 4.

In this case a first MRT segment image 5 of a first segmented volume region 6 is acquired with a central plane 7; a second MRT segment image 8 of a second segmented volume region 9 is acquired with a central plane 10; a third MRT segment image 11 of a third segmented volume region 12 is acquired with a central plane 13; a fourth MRT segment image 14 of a fourth segmented volume region 15 is acquired with a central plane 16; and a fifth MRT segment image 17 of a fifth segmented volume region 18 is acquired with a central plane 19. In this context the MRT segment images 5, 8, 11, 14 and 17 form the segmented volume regions 6, 9, 12, 18, which overlap to some extent. In order to capture the dental object 1, a patient's head 20 is positioned relative to the MRT apparatus 4 within a measurement volume 21 of the MRT apparatus 4 by means of, for example, a head holder and/or by means of a bite holder. Then the individual MRT segment images 5, 8, 11, 14 and 17 are taken one after the other by means of the MRT apparatus 4. A curved target surface 22 with respect to the MRT apparatus within the measurement volume 21 has already been fixed or is fixed by the user. The target surface 22 is shown as a dashed dotted line and extends as a central plane through the maxilla 2 and/or the mandible 3. The target surface 22 may also be curved in an occlusal direction, so that the target surface 22 corresponds to an averaged surface through the tooth axes of the individual teeth of the jaws 2 and 3. The image data of the MRT segment images 5, 8, 11, 14 and 17 are transmitted from the MRT apparatus 4 to a computer 23 and are represented graphically by means of a display device 24, such as a monitor. Connected to the computer 23 are the input means, such as a keyboard 25 and a mouse 26. The input means 25 and 26 allow the user to operate a virtual tool by means of a cursor 27. The display device 24 is used to display in a schematic representation 28 the defined segmented volume regions 6, 9, 12, 15 and 18 as well as the target surface 22 relative to the object 1. The schematic representation 28 allows the user, such as a dentist, to view more clearly the position of the segmented volume regions and the target surface 22 relative to the object. A two dimensional composite image 29 is created from the individual MRT segment images 5, 8, 11, 14 and 17 by means of the computer 23, wherein the MRT segment images 5, 8, 11, 14 and 17 are projected onto the target surface 22. In this case the composite image 29 corresponds to a conventional panoramic slice image from X-ray diagnostics, and the target surface 22 corresponds to the course of the sharp slice of a conventional panoramic slice image. In the present case the depth 30 of the first segmented volume region 6 is 25 mm. A width 31 of the first segmented volume region 6, which corresponds to the width of the first MRT segment image 5, is 100 mm. A length 32 of the first segmented volume region 6, which corresponds to the length of the first MRT segment image 5, is 250 mm.

REFERENCE NUMERALS 1 holder
2 maxilla
3 mandible
4 MRT apparatus
5 first MRT segment image
6 segmented volume region
7 central plane
8 second MRT segment image
9 second segmented volume region
10 central plane
11 third MRT segment image
12 third segmented volume region
13 central plane
14 fourth MRT segment image
15 fourth segmented volume region
16 central plane
17 fifth MRT segment image
18 fifth segmented volume region
19 central plane
20 patient's head
21 measurement volume
22 curved target surface
23 computer
24 monitor or display device
25 keyboard
26 mouse
27 cursor
28 a schematic representation
29 composite image
30 depth
31 width
32 length

We claim:
1. Method for capturing a dental object with an object volume with Magnetic Resonance Tomography (MRT) apparatus, wherein a plurality of MRT segment images, which depict the respectively defined segmented volume regions, are acquired by the MRT apparatus within a mea- surement volume of the MRT apparatus, wherein the segmented volume regions overlap no more than partially, wherein a target surface is defined or has been defined; generating a computer-aided two dimensional composite image from the individual MRT segment images, which corresponds to a two dimensional aggregate image through the target surface within the object volume of the dental object, is generated computer-aided, wherein prior to creating the MRT segment images, the position and the orientation of the MRT segment images relative to the MRT apparatus are fixed and wherein each of the segmented volume regions within the object volume is arranged in such a way that a central plane of the respective segmented volume region is arranged parallel to a tangent of the target surface.

2. Method according to claim 1, wherein a depth of each of the segmented volume regions is defined, wherein each segmented volume region is defined with respect to its position and orientation within the measurement volume.

3. Method according to claim 2, wherein the depth of the segmented volume region is between 0.5 mm and 30 mm.

4. Method according claim 1, wherein the target surface of the two dimensional composite image is a curved target surface, which extends through the maxilla or the mandible of a sample head or a preview image of the patient's head.

5. Method according to claim 4, wherein the target surface is planar in shape in a direction perpendicular to an occlusal plane of the maxilla or the mandible or in one direction is curved in shape, tracking a course of tooth axes of the maxilla or the mandible.

6. Method according to claim 4, wherein the composite image corresponds to or simulates a conventional X-ray panoramic slice image.

7. Method according to claim 1, wherein the target surface of the composite image corresponds to or simulates a course of a sharp slice of a conventional X-ray panoramic slice image.

8. Method according to claim 1, wherein each of the segmented volume regions is arranged in such a way that a direction of the lowest resolution of the respective MRT segment image is arranged orthogonal to the target surface.

9. Method according to claim 1, wherein the number, the position or the orientation of the segmented volume regions are varied by means of an optimization method, until an error size falls below a fixed tolerance value.

10. Method according to claim 1, wherein prior to creating the MRT segment images the number of MRT segment images, the position or the orientation of the MRT segment images relative to the MRT apparatus are defined by a user, wherein the position and the orientation of the segmented volume regions of the MRT segment images relative to the MRT apparatus are defined by a virtual tool.

11. Method according to claim 1, wherein a sample head comprising a sample maxilla or a sample mandible is displayed in schematic form by a display device, wherein the defined segmented volume regions and their arrangement relative to the sample head or the defined target surface relative to the sample head are shown by means of a graphic representation.

12. Method according to claim 11, wherein the created composite image and the sample head are shown simultaneously on the display device with the graphic representation of the individual segmented volume regions or with the defined target surface.

13. Method according to claim 1, wherein each MRT segment image consists of a single MRT slice image or a stack of several MRT slice images.

14. Method according to claim 1, wherein in all of the MRT segment images the spatial position of the dental object relative to the measurement volume of the MRT apparatus remains the same.

* * * * *